US00PP10202P

United States Patent [19]

Howard

[11] Patent Number: Plant 10,202

[45] Date of Patent: Jan. 20, 1998

[54] SCAEVOLA PLANT NAMED 'OUTBACK MINI PINK FAN'

[75] Inventor: Eric Howard, Lilydale, Australia

[73] Assignee: Koala Blooms Pty. Ltd., Mordialloc, Australia

[21] Appl. No.: 694,171

[22] Filed: Aug. 8, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,929 8/1992 Rother ..... Plt./68.1

*Primary Examiner*—Howard J. Locker
*Assistant Examiner*—Kent L. Bell
*Attorney, Agent, or Firm*—C. A. Whealy

[57] ABSTRACT

A distinctive cultivar of Scaevola plant named 'Outback Mini Pink Fan', characterized by its mounded spreading habit; rapid growth rate; freely branching habit; numerous flowers per lateral branch; and light pink flowers.

2 Drawing Sheets

The present invention relates to a new and distinct cultivar of Scaevola plant, botanically known as *Scaevola albida*, and hereinafter referred to by the cultivar name 'Outback Mini Pink Fan'.

The new cultivar originated from a cross made by the inventor of two plants of the species *Scaevola albida*. The cultivar 'Outback Mini Pink Fan' was discovered and selected by the inventor as a flowering plant within the progeny of the stated cross in a controlled environment in Kalorama, Victoria, Australia.

Subsequent asexual reproduction of the new cultivar by terminal cuttings taken at Montrose, Victoria, Australia, has shown that the unique features of this new Scaevola are stable and reproduced true to type in successive generations of asexual reproduction.

The following traits have been repeatedly observed and are determined to be the unique characteristics of 'Outback Mini Pink Fan'. These characteristics in combination distinguish the new Scaevola as a new and distinct cultivar:

1. Mounded spreading plant habit that is suitable for ground covers or hanging basket containers.
2. Rapid growth rate.
3. Freely branching habit.
4. Numerous flowers per lateral branch.
5. Light pink flowers.

In contrast to the parents of the new Scaevola, plants of 'Outback Mini Pink Fan' have light pink flowers compared to the white or mauve-colored flowers of plants of the species *Scaevola albida*.

The new Scaevola has not been observed under all possible environment conditions. The phenotype may vary significantly with variations in environment such as temperature, light level and daylength, without, however, any variance in genotype.

The accompanying colored photographs illustrate the overall appearance and flower color of the new Scaevola, showing the colors as true as it is reasonably possible to obtain in colored reproductions of this type.

The first photograph comprises a top perspective view of a typical plant of the new Scaevola.

The second photograph comprises a close-up view of typical flowers of the new Scaevola.

The flower color in these photographs may appear different from the actual flower color due to light reflectance.

The following observations, measurements, values, and comparisons describe plants grown in Montrose, Victoria, Australia, under outdoor conditions with day temperatures ranging from 10° to 30° C., night temperatures ranging from 5° to 22° C., and light levels ranging from 5,000 to 9,000 footcandles. Color references are made to The Royal Horticultural Society Colour Chart except where general terms of ordinary dictionary significance are used.

Classification:

*Botanical.*—*Scaevola albida* cultivar Outback Mini Pink Fan.

*Commercial.*—Scaevola.

Parentage:

*Male or pollen parent.*—*Scaevola albida.*

*Female or seed parent.*—*Scaevola albida.*

Propagation:

*Type.*—By cuttings.

*Time to initiate and develop roots.*—Summer: 15 to 30 days at temperatures of 25° C. Winter: 20 to 30 days at temperatures of 20° C.

*Rooting habit.*—Numerous, fibrous, and freely branching.

Plant description:

*General appearance.*—Mounded, spreading herbaceous plant, suitable for hanging basket containers or as a ground cover. Lateral stems may be semi-upright, pendulous or prostrate. Appropriate for 12.5 pots to 25-cm hanging basket containers. To produce a 15-cm finished flowering plant from rooted cuttings, 16 to 20 weeks are required depending on temperature and light level.

*Plant height.*—About 30 cm from soil level to top of plant plane.

*Branching.*—Relatively freely branching, typically 3 to 6 lateral branches develop when the terminal apex is removed (pinched). Lateral branches are typically 4 to 20 cm in length.

*Growth rate.*—Rapid.

*Vigor.*—Moderate.

*Foliage description*—Arrangement: Alternate, single. Quantity: 10 to 40 per lateral branch. Leaf shape: Spatulate. Leaf apex: Obtuse. Leaf base: Cuneate. Leaf margin: Serrated. Leaf aspect: Flat. Leaf length: 1 to 4 cm. Leaf width: 0.5 to 2 cm. Leaf texture: Smooth, slightly pubescent on adaxial surface. Leaf attachment: Sessile. Leaf color: Young leaves: Adaxial surface: 138A. Abaxial surface: 137D. Fully expanded leaves: Adaxial surface: 137B. Abaxial surface: 137C. Venation: Adaxial surface: Inconspicuous. Abaxial surface: 138D.

Flower description:

*Flower type and shape.*—Semi-circular, fan-shaped flowers with five petals fused at the base to form a tubular flower throat. Flower throat open along the upper side exposing reproductive organs. Flowers last on the plant for 2 to 3 weeks and about 1 week as a fresh cut flower. Flowers self-cleaning.

*Flower arrangement.*—Flowers arise from leaf axils with one flower per axil. Flowers sessile.

*Natural flowering season.*—Natural flowering season is late spring to fall. Plants flower continuously during this period.

*Quantity of flowers.*—10 to 30 per lateral stem.

*Flower diameter.*—About 2 cm.

*Fragrance.*—Very faint, nectar sweet.

*Petals.*—Shape: Elliptic. Apex: Obtuse. Margin: Entire. Length: 8 to 12 mm. Width: 3 to 5 mm. Color: When opening: 55C. Adaxial surface: 55B with lighter pink margin and base. Color fades to 55D with subsequent development. Abaxial surface: 55C. After senescence: 56B.

*Flower bud.*—Shape: Fusiform. Length: 7 to 10 mm. Diameter: 1 to 2 mm. Color: 56A and 10D.

*Sepals.*—Quantity: Five. Shape: Broadly triangular. Apex: Bluntly pointed. Margin: Ciliate. Texture: Smooth. Color: 144A.

*Reproductive organs.*—Stamens: Quantity: Five. Anther shape: Oblong. Anther size: About 1 mm. Anther color: 17D. Pollen color: White. Pistils: Quantity: One. Stigma shape: Bilobate. Stigma color: 144B. Style length: 6 to 7 mm. Style color: 79A and 177B.

Disease resistance: No resistance or susceptibility to diseases observed.

Seed production: Seed production is typically not observed.

It is claimed:

1. A new and distinct Scaevola plant named 'Outback Mini Pink Fan', as illustrated and described.

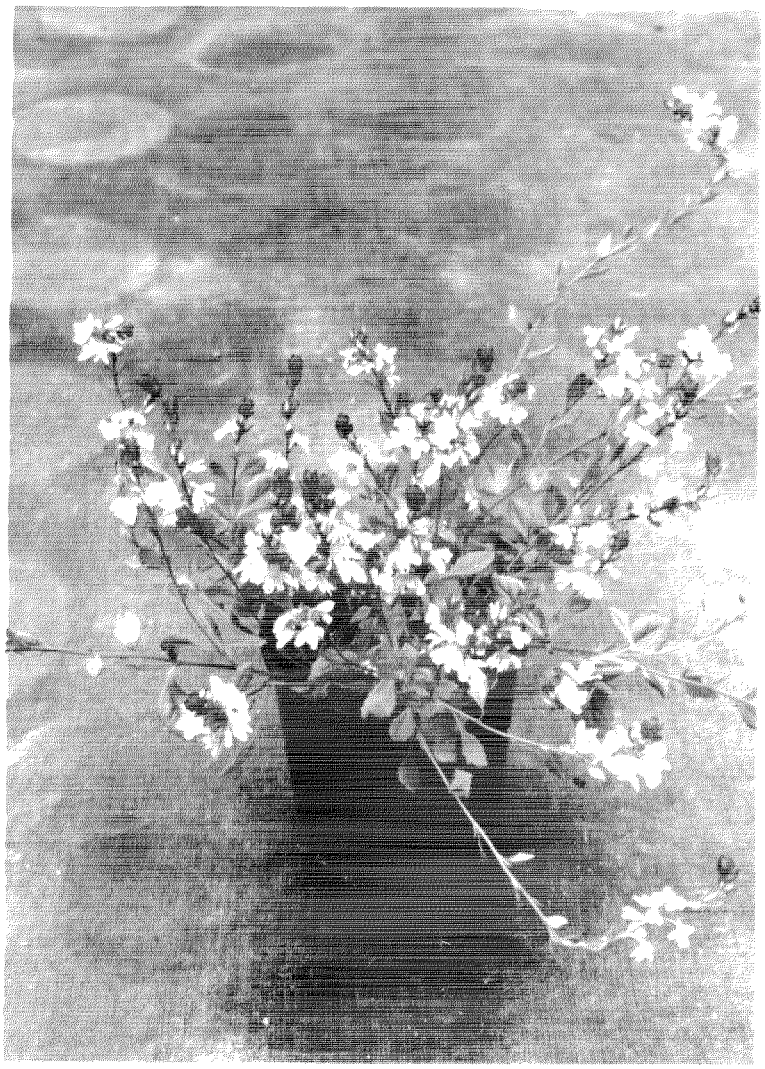

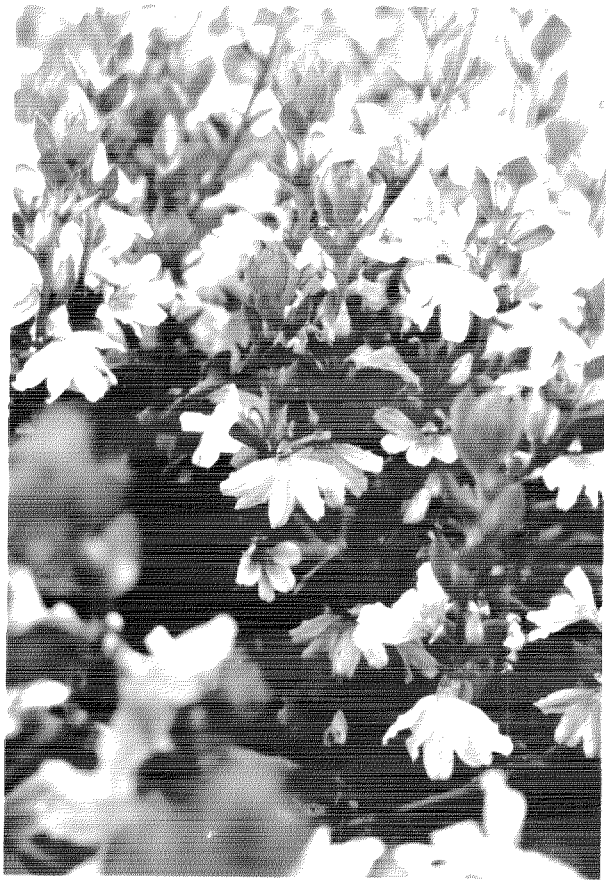

* * * * *